(12) United States Patent
Arai et al.

(10) Patent No.: US 7,691,398 B2
(45) Date of Patent: Apr. 6, 2010

(54) HAIR TREATMENT COMPOSITION COMPRISING COMPOSITE PARTICLES OF CLAY AND CHARGED ORGANIC MOLECULE

(75) Inventors: Takeshi Arai, Osaka (JP); Mark Edward Baker, Wirral (GB); Colin Christopher Giles, Bangkok (TH)

(73) Assignee: Unilever Home & Personal Care USA division of Conopco, Inc., Chicago, IL (US)

( * ) Notice: Subject to any disclaimer, the term of this patent is extended or adjusted under 35 U.S.C. 154(b) by 877 days.

(21) Appl. No.: 10/497,889

(22) PCT Filed: Nov. 12, 2002

(86) PCT No.: PCT/EP02/12627

§ 371 (c)(1),
(2), (4) Date: Jan. 6, 2005

(87) PCT Pub. No.: WO03/047541

PCT Pub. Date: Jun. 12, 2003

(65) Prior Publication Data

US 2005/0112074 A1  May 26, 2005

(30) Foreign Application Priority Data

Apr. 12, 2001 (EP) ................... 01310130
Sep. 4, 2002 (GB) ................... 0220578.9

(51) Int. Cl.
*A61K 8/02* (2006.01)
(52) U.S. Cl. ..................................... 424/401
(58) Field of Classification Search ........................ None
See application file for complete search history.

(56) References Cited

U.S. PATENT DOCUMENTS

| 3,876,760 | A | | 4/1975 | Nersesian ............... 424/70.13 |
| 4,390,033 | A | | 6/1983 | Khalil et al. |
| 5,112,603 | A | | 5/1992 | Nadolsky et al. |
| 5,786,381 | A | | 7/1998 | Franklin et al. |
| 5,814,323 | A | * | 9/1998 | Lyle ........................... 424/401 |
| 5,902,591 | A | | 5/1999 | Herstein |
| 5,968,491 | A | | 10/1999 | Richardson |
| 6,399,690 | B2 | | 6/2002 | Lan et al. ..................... 524/445 |
| 6,585,986 | B2 | * | 7/2003 | Matsuzaki et al. .......... 424/401 |
| 2002/0034486 | A1 | * | 3/2002 | Midha et al. ................ 424/70.2 |
| 2002/0188060 | A1 | * | 12/2002 | Okada et al. ................. 524/589 |

FOREIGN PATENT DOCUMENTS

| DE | 40 20 272 A1 | 1/1992 |
| EP | 0 099 987 | 2/1984 |
| EP | 0 370 764 | 5/1990 |
| EP | 0 379 590 A1 | 8/1990 |
| EP | 0 500 941 A1 | 9/1992 |
| EP | 0 726 246 A1 | 8/1996 |
| EP | 0 823 250 A2 | 2/1998 |
| EP | 1 317 917 | 6/2003 |
| EP | 1 475 070 A1 * | 11/2004 |
| WO | 99/25312 | 5/1999 |
| WO | 02/19976 A1 | 3/2002 |
| WO | 02/087524 | 11/2002 |
| WO | 03/047541 | 6/2003 |
| WO | 2004/022011 | 3/2004 |

OTHER PUBLICATIONS

International Search Report Application No. PCT/EP 02/12627 mailed Mar. 4, 2003.
Database WPI, Derwent Publ. Ltd., AN 1979 —48186 B; XP002197918 & JP 54 063132 A (Shiseido Co. Ltd.), May 21, 1979, (Abstract).
Database CA Chemical Abstracts Service, Columbus, Ohio, Database Accession No. 80:124578, 54; Markland, W.R.: "Laponite Synthetic Clays", Cosmetics and Perfumery (1974), 89 (1), 24 (Abstract).
Search Report under Section 17, Application No. GB 0220578.9 dated Feb. 20, 2003.
WPI Abstract Accession No. 1993-339612/43 & JP05246824A (Shiseido), Sep. 24, 1993, (Abstract).
PCT International Search Report in an PCT application PCT/EP 03/09224.
GB Search Report in an GB application GB 0220580.8.
Co-pending Application: Applicant: Giles et al., U.S. Appl. No. 10/526,850, filed Mar. 2, 2005.

* cited by examiner

*Primary Examiner*—Robert A Wax
*Assistant Examiner*—Bethany Barham
(74) *Attorney, Agent, or Firm*—Karen E. Klumas

(57) ABSTRACT

A hair treatment composition comprising an aqueous dispersion of composite particles, said particles comprising: i) a clay with a net surface charge, and ii) a charged organic molecule comprising at least 6, preferably at least 11, more preferably at least 17 carbon atoms, wherein the charge on the charged organic molecule is opposite to the net surface charge of the clay, said hair treatment composition further comprising one or more suitable hair treatment ingredients.

10 Claims, No Drawings

HAIR TREATMENT COMPOSITION COMPRISING COMPOSITE PARTICLES OF CLAY AND CHARGED ORGANIC MOLECULE

TECHNICAL FIELD

The present invention relates to hair treatment compositions comprising aqueous dispersions of composite particles and processes for their preparation. Water based hair treatment compositions containing particles according to the invention, such as conditioner and shampoo compositions, provide specific feel benefits to hair.

BACKGROUND OF THE INVENTION

The way their hair feels is very important to consumers of hair products. Desirable feel characteristics for hair include smoothness, softness, slippery feel when wet, ease of comb (both in the wet and dry states), no static, moisturisation and cleanness.

Compositions which provide improved feel to the hair are well known in the art and include rinse off products such as conditioners, shampoos, shower-gels, lotions and the like. These compositions improve feel characteristics of hair by depositing one or more of a wide variety of benefit agents, such as conditioning agents, onto the hair. However, such compositions can also lead to the hair looking and feeling heavy, greasy, dull and lifeless, due to the presence and/or accumulation of benefit and/or deposition agents on the surface of the hair. The clean feel of the hair can then be restored by removing these agents, for example by use of a so-called cleansing shampoo. However, the hair can then feel difficult to comb, harsh and lacks the benefits bestowed by the benefit agents just removed. In particular, such shampooing can leave the hair in a tangled and generally unmanageable state. Once the hair dries, it is often dry, rough, lustreless, or frizzy due to removal of the hair's natural oils and other conditioning and moisturizing components. The hair can further be left with increased levels of static upon drying, which can interfere with combing and result in a condition commonly referred to as "fly-away hair", or contribute to an undesirable phenomena of "split ends", particularly for long hair.

There remains a clear need for hair treatment compositions which are capable of imparting smoothness, moisturisation, ease of comb, etc, whilst also leaving the hair feeling clean, light and airy.

PRIOR ART

JP05/246,824 (Shiseido Co Ltd) discloses a hair cosmetic which is a water-in-oil emulsion containing an organically modified clay mineral (prepared by treating a water swelling clay with a nonionic surfactant and a cationic surfactant), a water-soluble high molecular weight substance and a high molecular weight silicone. The benefits claimed are smooth feel, lustre, firmness and flexibility to hair.

U.S. Pat. No. 5,786,381 (Franklin et al) describes cosmetic compositions containing hydroxy materials, including layered double hydroxides for treating skin, which may be delivered from a shampoo. The hydroxide is combined with an anionic form of a skin benefit agent which may be lactic acid, glycolic acid or alpha-hydroxycaprylic acid.

WO 02 19976 A (Procter and Gamble Co) describes hair conditioning compositions containing a high melting point fatty compound, a particle and a) an amidoamine and an acid or b) a cationic conditioning agent and a low melting point oil. The particle can be mica, silica, mud or clay. The benefit claimed is improved texture when spread on hands and/or hair.

EP 0726246 A (Rheox International) describes a quaternary ammonium composition comprising a blend of a liquid diluent and a quaternary ammonium compound. One suggested application is as reaction materials in the manufacture of organoclays.

It has now surprisingly been found that hair treatment compositions comprising an aqueous dispersion of composite particles, said composite particles comprising a clay with a net surface charge and a charged organic compound, said hair treatment composition further comprising one or more suitable hair treatment ingredients give benefits of smoothness, reduced friction, moisturisation and slippery feel whilst leaving the hair feeling clean, light and airy.

DEFINITION OF THE INVENTION

According to a first aspect of the invention, there is provided a hair treatment composition comprising an aqueous dispersion of composite particles, said particles comprising:
  i) a clay with a net surface charge, and
  ii) a charged organic molecule comprising at least 6, preferably at least 11, more preferably at least 17 carbon atoms, wherein the charge on the charged organic molecule is opposite to the net surface charge of the clay, said hair treatment composition further comprising one or more suitable hair treatment ingredients.

According to a second aspect of the invention, there is provided a process for the preparation of composite particles, wherein the clay is mixed with the charged organic molecule, the clay preferably being added to an aqueous dispersion of the charged organic molecule.

According to a third aspect of the invention, there is provided a process for the preparation of a hair treatment composition comprising the steps of:
  (i) preparing an aqueous dispersion of composite particles, and
  (ii) combining the aqueous dispersion of composite particles with suitable hair treatment ingredients in a compatible aqueous carrier.

DETAILED DESCRIPTION OF THE INVENTION

Suitable Hair Treatment Compositions

Hair treatment compositions include such compositions as shampoo, conditioner, gel, mousse, shower gel, lotion and serum. Such compositions must be water based; by water based is meant that the composition contains at least 20, preferably 35, most preferably 50 percent water by weight of the total composition. Hair treatment compositions are suitably wash off compositions. Particularly preferred composition forms are shampoos and post-wash conditioners. For sake of clarity, water forms the continuous phase in compositions of the invention, which may be in the form of an emulsion or particulate dispersion.

The Composite Particles

The composite particles according to the invention provide feel benefits to hair when used in water based hair treatment compositions such as conditioner and shampoo compositions.

The composite particles essentially comprise a clay, which has a net charge on its layer surface, and a charged organic molecule.

In order to achieve good deposition onto hair, it is preferred if the particles according to the invention have a volume-based median particle diameter ($D_{0.5}$) of greater than 1, preferably greater than 2, more preferably greater than 3 and most preferably greater than 4 microns, and in order to achieve a stable formulation, the particles suitably have a volume-based median particle diameter ($D_{0.5}$) of less than 100, preferably less than 50, more preferably less than 19, more preferably less than 17 and most preferably less than 10 microns. For the sake of clarity, each upper limit can be combined with each lower limit to define suitable volume-based median particle diameter ranges. Volume-based median particle diameters can be determined using a Malvern Mastersizer (Malvern Instruments, UK).

The composite particles according to the invention are hydrophobic in character. The hydrophobicity is such that the particles can be dispersed in water to form an aqueous dispersion.

The said aqueous dispersion of composite particles is preferably substantially free from nonionic surfactant.

The Clay

The clay which is used in the present invention can be any suitable clay material known in the art. In general, the term clay refers to a composition comprising fine particles which have a net electrostatic charge (i.e., positive or negative) on at least one surface. Preferably, the clay has a layered structure comprising sheets of coordinated cations, wherein the cations form tetrahedra or octahedra with close packed oxygens and hydroxyl groups. The surface charge is usually balanced by the presence of charge balancing ions (sometimes called exchangeable ions) which are usually present between the layers of the clay and at the edges of the layers.

A suitable clay for the invention is an anionic clay. The term anionic clays and related terms, as used herein, refer to clays which are negatively charged at their layer surface. In this embodiment, the composite particles are formed with a cationic charged organic molecule, which is in addition to and separate from any charge balancing cations which may be present.

The clay may be a natural, synthetic or chemically modified clay. Preferably, the layers of the clay comprise hydrous sheets of octahedrally coordinated aluminium, magnesium or iron, or of tetrahedrally coordinated silicon. The arrangement of octahedrally coordinated cations to coordinating anions in the clay sheets may be dioctahedral or trioctahedral. The charge balancing ions are cations at the layer surfaces and anions at the edges and may be those occurring naturally in the clay or by exchange using ion exchange techniques. The charge balancing cations of the anionic clays employed in the composite particles of the invention will contain cationic counterions such as protons, sodium ions, potassium ions, calcium ions, magnesium ions, and the like.

Preferred anionic clays are 2:1 phyllosilicates, in which the clay layers comprise two tetrahedral sheets to one octahedral sheet. Preferred 2:1 phyllosilicates are smectite clays.

Other suitable clays have a 1:1 phyllosilicate structure, with an assemblage of one tetrahedral to one octahedral coordinated sheet in the clay layers.

Smectite clays, used in laundry compositions are, for example, disclosed in U.S. Pat. Nos. 3,862,058, 3,948,790, 3,954,632 and 4,062,647 and in EP-A-299,575 and EP-A-313,146, all in the name of Procter & Gamble Company.

The term smectite clays herein includes both the clays in which aluminium oxide is present in a silicate lattice and the clays in which magnesium oxide is present in a silicate lattice. Typical smectite clay compounds include the compounds having the general formula $Al_2(Si_2O_5)_2(OH)_2.nH_2O$ and the compounds having the general formula $Mg_3(Si_2O_5)_2(OH)_2.nH_2O$, and derivatives thereof, for example in which a proportion of the aluminium ions are replaced with magnesium ions or a proportion of the magnesium ions are replaced with lithium ions and/or some of the hydroxyl ions are replaced by fluoride ions; the derivatives may comprise a further metal ion to balance the overall charge.

Specific examples of suitable smectite clays include those selected from the classes of the montmorillonites, hectorites, volchonskoites, nontronites, saponites, beidelites and sauconites, particularly those having an alkali or alkaline earth metal ion within the crystal lattice structure. Particularly preferred are hectorites, montmorillonites, nontronites, saponites, beidelites, sauconites and mixtures thereof. More preferably the clay is a synthetic hectorite.

The cation exchange capacity (CEC) of a clay is a well known parameter and may be determined by well established analytical techniques, including by electrodialysis, by exchange with ammonium ion followed by titration or by a methylene blue procedure, all as fully described in Grimshaw, "The Chemistry and Physics of Clays", pp. 264-265, Interscience (1971). It is customary to measure the cation exchange capacity of a clay in terms of milliequivalents per 100 g of dry clay (meq/100 g).

Preferred anionic clays for use in the present invention have a cation exchange capacity of from 0.7 meq/100 g to 150 meq/100 g. Particularly preferred are clays having a cation exchange capacity of from 30 meq/100 g to 100 meq/100 g.

The clays preferably have a volume-based median particle diameter ($D_{0.5}$) from 0.001 µm to 80 µm, more preferably from 0.01 µm to 50 µm and most preferably 0.02 µm to 20 µm. Particle diameters can be determined using a Malvern Mastersizer (Malvern Instruments, UK).

Examples of synthetic hectorites useful in the present invention include those products sold under the trade names Laponite RD, Laponite RDS, Laponite XLG, Laponite XLS, Laponite D, Laponite DF, Laponite DS, Laponite S and Laponite JS (all from Southern Clay products, Texas, USA, a subsidiary of Rockwood).

Examples of montmorillonites (also known as bentonites), which are suitable for use in the present invention include: Gelwhite GP, Gelwhite H, Gelwhite L, Mineral Colloid BP, Mineral Colloid MO, Gelwhite MAS 100 (sc), Gelwhite MAS 101, Gelwhite MAS 102, Gelwhite MAS 103, Bentolite WH, Bentolite L10, Bentolite H, Bentolite L, Permont SX10A, Permont SC20, and Permont HN24 (Southern Clay Products, Texas, USA); Bentone EW and Bentone MA (Dow Corning); Bentonite USP BL 670 and Bentolite H4430 (Whitaker, Clarke & Daniels); Clarit 100 G1 and Clarit 1100 G1 (calcium bentonites from Süd Chemie AG); and Volclay 2 (sodium bentonite from Süd Chemie AG).

Clays may be used in the present invention either singly or in combination with one or more other clays. If a mixture of clays is used, however, it is preferred that either all of the clays are anionic or all of the clays are cationic. However, mixtures of cationic and anionic clays may be used.

Clays may be used as obtained from the supplier and may contain conventional additives such as, for example, disintegrating agents (also known as peptisers) and water of hydration. The clays may be used in their natural state or in a purified or semi-purified form, for example with the removal of mineral impurities.

Another suitable clay for the invention is a cationic clay. The term cationic clays and related terms, as used herein, refers to clays which are themselves cationic in nature i.e., the clays themselves are positively charged at their layer surfaces. In this embodiment, the composite particles are formed with an anionic charged organic molecule which is in addition to and separate from any charge balancing anions which may be present in the clay.

Preferred examples of cationic clays are the natural or synthetic layered double hydroxide (LDH) clays. For instance, layered double hydroxides include compounds of formula

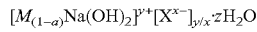

$[M_{(1-a)}Na(OH)_2]^{y+}[X^{x-}]_{y/x} \cdot zH_2O$ where M is selected from divalent metal ions and lithium; N is a trivalent metal ion; X is an anion of charge x−; y+ is the net charge on the mixed metal hydroxide cation; and when M is a divalent metal ion, "a" is a number from 0.17 to 0.5 and y=a; and when M is lithium "a" is a number from 0.67 to 0.75 and y=(2a−1); and z is a number from 0 to 10.

In these structures, the metal ions occur in layers in which the metal ions are connected together through the OH groups and the anions X, are located in interlayers between layers of metal ions. It is known that X can undergo ion exchange to be replaced by other anions e.g. organic anions. Various applications for these types of hydroxy materials have been described in the scientific literature, notably including their use as chemical catalysts.

A preferred LDH is hydrotalcite, which has the formula:

$(Mg)_2(Al)_4(OH)_{12} \cdot (CO_3)_2 \cdot 4H_2O$

Examples of cationic clays in the hydrotalcite category include Pural MG30, Pural MG50, Pural MG70 (from Condea Chemie GmbH, Hamburg, Germany). Hydrotalcites commercially available include Sorbacid EXM 911 and Hycite EM 713 (from Süd Chemie AG). Other examples of layered double hydroxides are $Mg_4Al_2(OH)_{12}(SO_4)_{0.8} \cdot xH_2O$ Magaldrate (Guilini) and $Mg_4Al_4(OH)_{12}Cl_2 \cdot xH_2O$ mixed metal hydroxide (Dow Chemicals). Bayerite is also a suitable cationic clay.

Preferred cationic clays for use in the present invention have an ion exchange capacity of from 0.7 meq/100 g to 250 meq/100 g. Particularly preferred are clays having an ion exchange capacity of from 30 meq/100 g to 200 meq/100 g.

In the compositions of the invention, the clay is advantageously present in the form of a dispersion (for example a sol or gel) or a suspension of the clay particles.

The Charged Organic Molecule

The charged organic molecule bears a charge which is opposite to that of the surface charge of the clay layer, and is derived from an organic ionic compound e.g. a salt. Any suitable charged organic species may be used. The charged organic molecule may be cationic or anionic, depending on the charge type of the clay. Thus, a cationic charged organic molecule is used with an anionic clay and an anionic charged organic molecule is used with a cationic clay. The charged organic molecule can be a zwitterionic or an amphoteric compound. For the sake of clarity, when such a zwitterionic or amphoteric compound is used, the pH of the composition must be adjusted so as to achieve a charge on the zwitterionic or amphoteric compound, which is opposite to that of the surface charge of the clay layer. It will be well known to a person skilled in the art how to suitably adjust the pH of the composition so as to achieve a charge on the zwitterionic or amphoteric compound.

The charged organic molecule comprises an organic molecule with one or more charged substituents. By organic is meant any molecule containing carbon. The charged organic molecule comprises at least 6, preferably at least 11 and more preferably at least 17 carbon atoms. For the avoidance of doubt, the charged organic molecule is not the same as and is separate from the charge balancing ions, which are naturally present in the clay itself.

In order to form the composite particles, the charged organic molecule must be mixed with the clay. Suitably, the charged organic molecule will be added in the form of a neutral salt.

The charged organic molecule preferably contains at least one straight chain or branched alkyl group or carbon based chain, said alkyl group preferably comprises 3 to 22, more preferably 6 to 22 and most preferably 12 to 22 carbon atoms.

The charged organic molecule can also be a cationic or anionic, semi-permanent dye but preferably is not capable of imparting a colour to hair.

Positively charged organic molecules are preferably selected from the cations of cationic surfactants, cationic polymers and fatty amines used in combination with an acid; negatively charged organic molecules are preferably selected from the anions of anionic surfactants, anionic polymers and polyelectrolytes. For the sake of clarity, dyes are not included in these preferred subsets.

The weight ratio of the charged organic molecule to the clay is from 0.05:1 to 20:1, preferably from 0.1:1 to 10:1, and most preferably from 0.2:1 to 5:1. For the avoidance of doubt, the weight of the charged organic molecule mentioned in the above ratio refers to the weight of the charged organic molecule and excludes any counterion in the neutral salt from which the charged molecule may originate.

Cationic Charged Organic Molecules

When an anionic clay is used, the charged organic molecule is preferably selected from the cation of a cationic surfactant, a cationic polymer and a fatty amine used in combination with an acid.

The preferred cationic charged organic molecule is the cation of a cationic surfactant.

Cationic surfactants useful in compositions of the invention contain amino or quaternary ammonium hydrophilic moieties which are positively charged in aqueous solutions.

Examples of suitable cationic surfactants are those corresponding to the general formula (I):

$[N(R_1)(R_2)(R_3)(R_4)]^+(X)^-$     (formula I)

in which $R_1$ and $R_2$ are independently selected from (a) an aliphatic group of from 1 to 22, preferably 8 to 22, most preferably 16 to 22 carbon atoms, or (b) an aromatic, alkoxy, polyoxyalkylene, alkylamido, hydroxyalkyl, aryl or alkylaryl group having up to 22 carbon atoms;

$R_3$ and $R_4$ and are independently selected from (a) an aliphatic group of from 1 to 12, preferably 1 to 6, most preferably 1 to 3 carbon atoms, or (b) an aromatic, alkoxy, polyoxyalkylene, alkylamido, hydroxyalkyl, aryl or alkylaryl group having up to 12, preferably up to 6, most preferably up to 3 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

Preferably, $R_1$ of formula (I) is independently selected from
  (a) an aliphatic group of from 1 to 22, preferably 8 to 22, most preferably 16 to 22 carbon atoms, or
  (b) an aromatic, alkoxy, polyoxyalkylene, alkylamido, hydroxyalkyl, aryl or alkylaryl group having up to 22 carbon atoms; and $R_2$, $R_3$ and R4 and are independently selected from
  (a) an aliphatic group of from 1 to 12, preferably 1 to 6, most preferably 1 to 3 carbon atoms, or
  (b) an aromatic, alkoxy, polyoxyalkylene, alkylamido, hydroxyalkyl, aryl or alkylaryl group having up to 12, preferably up to 6, most preferably up to 3 carbon atoms; and X is a salt forming anion.

More preferably, R1 of formula (I) is C16 to C22 and R2, R3 and R4 are methyl groups.

Examples of suitable cationic surfactants include quaternary ammonium compounds, particularly quaternary ammonium compounds comprising a single straight or branched alkyl chain and three methyl groups in which said alkyl chain comprises 16 to 22 carbon atoms.

Suitable quaternary ammonium compounds include cetyltrimethylammonium chloride (CTAC), behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, tallowtrimethylammonium chloride, cocotrimethylammonium chloride, PEG-2 oleylammonium chloride, and salts of these, where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18.

Further suitable cationic surfactants include didodecyldimethylammonium chloride and dioctadecyldimethylammonium chloride.

Mixtures of any of the foregoing materials may also be suitable.

Preferred quaternary ammonium salts are behenyltrimethylammonium chloride (BTAC) such as Genamin KDMP supplied by Clariant and cetyltrimethylammonium chloride (CTAC), Such as Arquad 16/29 supplied by Akzo Nobel.

Further suitable cationic systems are primary, secondary, and tertiary fatty amines used in combination with an acid to provide the cationic species. The alkyl groups of such amines preferably have from 12 to 22 carbon atoms, and can be substituted or unsubstituted.

Particularly useful are amido substituted tertiary fatty amines, in particular tertiary amines having one $C_{12}$ to $C_{22}$ alkyl or alkenyl chain. Such amines, useful herein, include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachid amidopropyldiethylamine, arachidamidoethyldiethylamine, arachidamidoethyldimethylamine, diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

As stated previously, these amines are typically used in combination with an acid to provide the cationic species. The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to $H^+$ from the acid is preferably from about 1:0.3 to 1:1.2, and more preferably from about 1:0.5 to about 1:1.1.

Other suitable cationic charged organic molecules for use in the composite particles of the invention are cationic polymers.

These may be homopolymers or be formed from two or more types of monomers. The molecular weight of the polymer will generally be between 5,000 and 10,000,000, typically at least 10,000 and preferably from 100,000 to about 2,000,000 Da. The polymers will have cationic nitrogen containing groups such as quaternary ammonium or protonated amino groups, or a mixture thereof.

Suitable cationic nitrogen polymers are described in the CTFA Cosmetic Ingredient Directory, 3rd edition.

The cationic polymers can comprise mixtures of monomer units derived from amine- and/or quaternary ammonium-substituted monomer and/or compatible spacer monomers.

Suitable cationic polymers include, copolymers of 1-vinyl-2-pyrrolidine and 1-vinyl-3-methyl-imidazolium salts (CTFA name Polyquaternium-16); copolymers of 1-vinyl-2-pyrrolidine and dimethylaminoethyl methacrylate, (CTFA name Polyquaternium-11); cationic diallyl quaternary ammonium-containing polymers in particular(CTFA Polyquaternium 6 and Polyquaternium 7, mineral acid salts of amino-alkyl esters of homo- and co-polymers of unsaturated carboxylic acids as described in U.S. Pat. No. 4,009,256; cationic polyacrylamides (as described in WO95/22311).

Cationic polysaccharide polymers suitable for use in compositions of the invention include those with an anhydroglucose residual group, such as a starch or cellulose. Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other suitable cationic polysaccharide polymers include quaternary nitrogen-containing cellulose ethers (e.g. as described in U.S. Pat. No. 3,962,418), and copolymers of etherified cellulose and starch (e.g. as described in U.S. Pat. No. 3,958,581).

A particularly suitable type of cationic polysaccharide polymer that can be used is a cationic guar gum derivative, such as guar hydroxypropyltrimonium chloride (commercially available from Rhodia in their JAGUAR trademark series). Particularly preferred cationic polymers are JAGUAR C13S, JAGUAR C14, JAGUAR C15, JAGUAR C17 and JAGUAR C16 Jaguar CHT and JAGUAR C162.

Further suitable cationic charged organic molecules for use in the composite particles of the invention are cationic dyes. Suitable cationic dyes, which contain cationic charged organic molecules, include:

3-[(4-amino-6-bromo-5,8-dihydro-1-hydroxy-8-imino-5-oxo-2-naphtyl)amino]-N,N,N-trimethylanilinium chloride (CI 56059; Basic Blue No. 99—Trade name Arianor Steel Blue & Jaracol Steel Blue);

mixtures of: 8-[(4-amino-3-nitrophenyl)azo]-7-hydroxy-N,N,N-trimethyl-2-naphthaleneaminium chloride [Major]; 8-[(4-amino-2-nitrophenyl)azo]-7-hydroxy-N,N,N-trimethyl-2-naphthaleneaminium chloride [Minor] (Basic Brown No. 17—Arianor Sienna Brown & Jaracol Sienna Brown);

8-[(4-aminophenyl)azo]-7-hydroxy-N,N,N-trimethyl-2-naphthaleneaminium chloride(CI 12250; Basic Brown No. 16—Arianor Mahogany & Jaracol Mahogany);

3-[4,5-dihydro-3-methyl-5-oxo-1-phenyl-1H-pyrazol-4-yl) azo]-N,N,N-trimethylanilinium chloride (CI 12719; Basic Yellow No. 57—Arianor Straw Yellow & Jaracol Straw Yellow); and 7-Hydroxy-8-[(2-methoxyphenyl)azo]-N,N,N-trimethyl-2-naphthaleneaminium chloride (CI 12245; Basic Red No. 76—Arianor Madder Red & Jaracol Madder Red).

The dyes mentioned above are available from Warner Jenkinson Europe, Kings Lynn, Norfolk, UK. Jaracol dyes are available from James Robinson Dyes, Huddersfield, UK.

Other examples of suitable cationic dyes containing cationic charged organic molecules suitable for use in the invention include:

9-(dimethylamino)benzo[a]phenoxazin-7-ium chloride (CI 51175; Basic Blue No. 6);

di[4-(diethylamino)phenyl]-[4-(ethylamino)naphthyl]carbenium chloride (CI 42595; Basic Blue No. 7);

3,7-di-(dimethylaminophenothiazin-5-ium chloride (CI 52015; Basic Blue No. 9);

di[4-(dimethylamino)phenyl]-[4-(phenylamino)naphthyl] carbenium chloride (CI 44045; Basic Blue No. 26);

2[(4-(ethyl(2-hydroxyethyl)amino)phenyl)azo]-6-methoxy-3-methylbenzothiazolium methyl sulfate (CI 11154; Basic Blue No. 41);

bis[4-(dimethylamino)phenyl][4-(methylamino)phenyl]carbenium chloride (CI 42535; Basic Violet No. 1);

tris-[4-(dimethylamino)phenyl]carbenium chloride (CI 42555; Basic Violet No. 3);

2-[3,6-(diethylamino)dibenzopyranium-9-yl]benzoic acid chloride (CI 45170; Basic Violet No. 10);

di(4-aminophenyl)(4-amino-3-methylphenyl)carbenium chloride (CI 42510; Basic Violet No. 14);

1,3-bis[(2,4-diamino-5-methylphenyl)azo]-3-methylbenzene (CI 21010; Basic Brown No. 4);

1-[(4-amino-2-nitrophenyl)azo]-7-(trimethylammonio)-2-naphthol chloride (CI 12251; Basic Brown No. 17);

3,7-diamino-2,8-dimethyl-5-phenylphenazinium chloride (CI 50240; Basic Red No. 2);

1,4-dimethyl-5-[(4-(dimethylamino)phenyl)azo]-1,2,4-triazolium chloride (CI 11055; Basic Red No. 22);

2-[2-((2,4-dimethyoxyphenyl)amino)ethenyl]-1,3,3-trimethyl-3H-indol-1-ium chloride (CI 48055; Basic Yellow No. 11); and bis[4-(diethylamino)phenyl)phenylcarbenium hydrogen sulfate (1:1) (CI 42040; Basic Green No. 1).

Charged organic molecules which are the cationic species in the so-called Basic dyes are particularly suitable.

Anionic Charged Organic Molecules

The charged organic molecule is preferably selected from the anion of anionic surfactant, an anionic polymer and a polyelectrolyte, when a cationic clay is used.

The preferred anionic charged organic molecule is the anion of an anionic surfactant.

Examples of suitable anionic surfactants are the alkyl sulphates, alkyl ether sulphates, alkaryl sulphonates, alkanoyl isethionates, alkyl succinates, alkyl sulphosuccinates, alkyl phosphates, alkyl ether phosphates, alkyl carboxylates, alkyl ether carboxylates, alkyl ester carboxylates, N-alkyl sarcosinates, and alpha-olefin sulphonates, especially their sodium, magnesium, ammonium and mono-, di- and triethanolamine salts. The alkyl and acyl groups generally contain from 8 to 22, preferably 12 to 22 carbon atoms, and may be saturated or unsaturated and can contain, in addition to carbon and hydrogen atoms, ether linkages, and other groups such as amino and ester groups. The alkyl ether sulphates, alkyl ether phosphates and alkyl ether carboxylates may contain from 1 to 10 ethylene oxide or propylene oxide units per molecule.

Typical anionic surfactants for use in compositions of the invention include sodium oleyl sulpho succinate, ammonium lauryl sulphosuccinate, ammonium lauryl sulphate, sodium cocoyl isethionate, sodium lauryl isethionate and sodium N-lauryl sarcosinate, sodium lauryl sulphate, sodium lauryl ether sulphate(n)EO, (where n ranges from 1 to 3), ammonium lauryl sulphate, ammonium lauryl ether sulphate(n)EO, (where n ranges from 1 to 3), sodium heptadecyl sulphate, sodium and tetra decyl sulphate.

Further suitable anionic charged organic molecules are anionic polymers.

Examples of suitable anionic polymers are polyacrylates, cross-linked polyacrylates (for example Carbopol ETD 2001 supplied by Goodrich), hydrophobically modified polyacrylates (for example Carbopol 2623 supplied by Goodrich), polyalkylacrylates (for example Carbopol ETD 2020 supplied by Goodrich), polymethacrylates, polymethylvinylether/maleic anhydride (PVM/MA) copolymers (for example the Gantrez AN series supplied by ISP), alkyl esters of PVM/MA copolymers (for example, the Gantrez series supplied by ISP), monoester resins of PVM/MA copolymers (for example, the Gantrez ES series supplied by ISP), polymethylcarboxylates, polysulphonates and polyphosphates. Further suitable polymers are silicone glycol copolymers, such as DC Q2-5220 supplied by Dow Corning.

Further suitable anionic charged organic molecules for use in the composite particles of the invention are anionic dyes. Suitable anionic dyes, which contain anionic charged organic molecules, include azo dyes, xanthene dyes and dyes based on carbenium salts. Specific examples of dyes are:

6-hydroxy-5-[(4-sulfophenyl)azo]-2-naphthalenesulfonic acid disodium salt (CI 15985; Food Yellow No. 3);

2,4-dinitro-1-naphthol-7-sulfonic acid disodium salt (CI 10316; Acid Yellow No. 1; Food Yellow No. 1);

2-(2-quinolyl)-1H-indene-1,3(2H)-dione (mixture of mono- and disulfonic acid) (CI 47005; Food Yellow No. 13; Acid Yellow No. 3);

4,5-dihydro-5-oxo-1-(4-sulfophenyl)-4-[(4-sulfophenyl) azo]-1H-pyrazole-3-carboxylic acid trisodium salt (CI 19140; Food Yellow No. 4; Acid Yellow No. 23);

3',6'-dihydroxyspiro[isobenzofuran-1(3H),9-[9H]xanthen]-3-one disodium salt (CI 45350; Acid Yellow No. 73; D & C Yellow No. 8);

5-[(2,4-dinitrophenyl)amino]-2-phenylaminobenzene-sulfonic acid sodium salt (CI 10385; Acid Orange No. 3);
4-[(2,4-dihydroxyphenyl)azo]benzenesulfonic acid monosodium salt (CI 14270; Acid Orange No. 6);
4-[(2-hydroxy-1-naphthalenyl)azo]benzenesulfonic acid monosodium salt (CI 15510; Acid Orange No. 7);
4-[[3-[(2,4-dimethylphenyl)azo]-2,4-dihydroxyphenyl]azo]benzenesulfonic acid monosodium salt (CI 20170; Acid Orange No. 24);
4-hydroxy-3-[(4-sulfo-1-naphthalenyl)azo]-1-naphthalenesulfonic acid disodium salt (CI 14720; Acid Red No. 14);
7-hydroxy-8-[(4-sulfo-1-naphthalenyl)azo]-1,3-naphthalenedisulfonic acid trisodium salt (CI 16255; Ponceau 4R; Acid Red No. 18);
3-hydroxy-4-[(4-sulfo-1-naphthalenyl)azo]-2,7-naphthalenedisulfonic acid trisodium salt (CI 16185; Acid Red No. 27; Food Red 9);
5-amino-4-hydroxy-3-(phenylazo)-2,7-naphthalenedisulfonic acid disodium salt (CI 17200; Acid Red No. 33);
5-(acetylamino)-4-hydroxy-3-[(2-methylphenyl)azo]-2,7-naphthalenedisulfonic acid disodium salt (CI 18065; Acid Red No. 35);
3'-6'-dihyroxy-2',4',5',7'-tetraiodospiro[isobenzofuran-1(3H),9'-[9H]xanthen]-3-one disodium salt (CI 45430; Acid Red No. 51);
N-[6-(diethylamino)-9-(2,4-disulfophenyl)-3H-xanthen-3-ylidene]-N-ethylethaneamminium hydroxide, internal salt, sodium salt (CI 45100; Acid Red No. 52);
7-hydroxy-8-[[4-(phenylazo)phenyl]azo]-1,3-napthalenedisulfonic acid disodium salt (CI 27290; Acid Red No. 73);
2',4',5',7'-tetrabromo-3',6'-dihydroxyspiro[isobenzofurane-1(3H), 9'-[9H]-xanthen]-3-one disodium salt (CI 45380; Acid Red No. 87);
2',4',5',7'-tetrabromo-4,5,6,7-tetrachloro-3',6',-dihydroxyspiro[isobenzofuran-1(3H),9'-[9H]-xanthen]-3-one disodium salt (CI 45410; Acid Red No. 92);
3',6'-dihydroxy-4'5'-diiodospiro[isobenzofuran]-1(3H), 9'-(9H)-xanthen]-3-one disodium salt (CI 45425; Acid Red No. 95);
Benzenemethanaminium, N-ethyl-N-[4-[[4-[ethyl[(3-sulfophenyl)methyl]amino]phenyl](2-sulfophenyl)methylene]2,5-cyclohexadien-1-ylidene]-3-sulpho-, hydroxide, inner salt disodium salt (CI 42090; Acid Blue No. 9);
2,2'-[(9,10-dihydro-9,19-dioxo-1,4-anthracenediyl)diimino]bis[5-methyl]benzenesulphonic acid disodium salt (CI 61570; Acid Green No. 25);
N-[4-[[4-(diethylamino)phenyl](2-hydroxy-3,6-disulfo-1-napthalenyl)methylene]-2,5-cyclohexadien-1-ylidene]-N-methylmethaminium hydroxide internal salt, monosodium salt (CI 44090; Food Green No. 4; Acid Green No. 50);
N-[4-[[4-(diethylamino)phenyl](2,4-disulfophenyl) methylene]-2,5-cyclohexadien-1-ylidene]-N-ethylethanaminium hydroxide internal salt, sodium salt (CI 42045; Food Blue No. 3; Acid Blue No. 1);
N-[4-[[4-(diethylamino)phenyl](5-hydroxy-2,4-disulfophenyl)methylene]2,5-cyclohexadien-1-ylidene]-N-ethylethanaminium hydroxide internal salt, calcium salt (2:1) (CI 42051; Acid Blue No. 3);
1-amino-4-(cyclohexylamino)-9,10-dihydro-9,10-dioxo-2-anthracenesulfonic acid monosodium salt (CI 62045; Acid Blue No. 62);
2-(1,3-dihydro-3-oxo-5-sulfo-2H-indol-2-ylidene)-2,3-dihydro-3-oxo-1H-indole-5-sulfonic acid disodium salt (CI 73015, Acid Blue No. 74);
9-(2-carboxyphenyl)-3-[(2-methylphenyl)amino]-6-[(2-methyl-4-sulfophenyl)amino]xanthylium hydroxide internal salt, monosodium salt (CI 45190; Acid Violet No. 9);
2-[(9,10-dihydro-4-hydroxy-9,10-dioxo-1-anthracenyl)amino]-5-methylbenzenesulfonic acid monosodium salt (CI 60730; D & C Violet No. 2; Acid Violet No. 43);
bis[3-nitro-4-[(4-phenylamino)-3-sulfophenylamino]phenyl]sulfone (CI 10410; Acid Brown No. 13);
4-amino-5-hydroxy-3-[(4-nitrophenyl)azo]-6-(phenylazo)-2,7-naphthalenedisulfonic acid disodium salt (CI 20470; Acid Black No. 1);
3-hydroxy-4-[(2-hydroxynaphth-1-yl)azo]-7-nitro-1-naphthalenesulfonic acid chromium complex (3:2) (CI 15711; Acid Black No. 52);
3-[(2,4-dimethyl-5-sulfophenyl)azo]-4-hydroxy-1-naphthalenesulfonic acid disodium salt (CI 14700; Food Red No. 1; Ponceau SX; FD & C Red No. 4);
4-(acetylamino)-5-hydroxy-6-[(7-sulfo-4-[(4-sulfophenyl]azo]-1-naphthalenyl)azo]-1,7-naphthalene disulfonic acid tetrasodium salt (CI 28440, Food Black No. 1); and
3-hydroxy-4-(3-methyl-5-oxo-1-phenyl-4,5-dihydro-1H-pyrazol-4-ylazo)naphthalene-1-sulfonic acid sodium salt, chromium complex (Acid Red No. 195).

Charged anionic organic molecules, which are the anionic species in the so-called Acid dyes are particularly preferred.

Further Charged Organic Molecules

Further charged organic molecules are amphoteric or zwitterionic surfactants.

Examples of amphoteric and zwitterionic surfactants include, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in composite particles of the invention include lauryl amine oxide, cocodimethyl sulphopropyl betaine and preferably lauryl betaine, cocamidopropyl betaine and sodium cocamphopropionate.

Preparation of the Composite Particles and Hair Treatment Composition

The composite particles of the invention are prepared by mixing the charged organic molecule with the clay. The clay can be in a powdered form or as an aqueous suspension. The charged organic molecule is in the form of an aqueous dispersion. The charged organic molecule can be added to the clay, or the clay can be added to the charged organic molecule to form an aqueous dispersion of composite particles.

The aqueous dispersion of composite particles can be used to prepare a hair treatment composition by combining with remaining suitable hair treatment ingredients in a compatible aqueous carrier. In said preparation of a hair treatment composition, the aqueous dispersion of composite particles is prepared prior to addition to the remaining suitable hair treatment ingredients.

Hair treatment compositions in accordance with the invention are preferably formulated as products for the treatment of hair and subsequent rinsing.

Examples of hair treatment compositions that may be formed according to the present invention are a rinse off conditioner comprising a hair conditioning agent and a shampoo comprising a cleansing surfactant. By rinse off conditioner is meant a rinse off hair conditioner product, which is not a shampoo.

The weight of composite particles in the compositions of the invention is preferably from 0.01 to 20, more preferably 0.05 to 10 and most preferably 0.05 to 5 percent by weight of the total weight of the composition.

In a further aspect, the invention provides a method for treating hair, which comprises applying to the hair a hair treatment composition comprising an aqueous dispersion of composite particles.

In another aspect, the invention provides a method for modifying the feel of hair, which comprises applying to the hair a hair treatment composition comprising an aqueous dispersion of composite particles.

In another aspect, the invention provides a use of a hair treatment composition comprising an aqueous dispersion of composite particles to modify the feel of hair.

Hair Treatment Compositions

Compositions in accordance with the invention are preferably formulated as products for the treatment of hair and subsequent rinsing.

Shampoo Compositions

Shampoo compositions preferably comprise one or more cleansing surfactants which are cosmetically acceptable and suitable for topical application to the hair. Further surfactants may be present as emulsifiers.

Suitable cleansing surfactants, are selected from anionic, amphoteric and zwitterionic surfactants, and mixtures thereof. The cleansing surfactant may be the same surfactant as the emulsifier, or may be different.

Anionic Cleansing Surfactant

Shampoo compositions according to the invention will typically comprise one or more anionic cleansing surfactants which are cosmetically acceptable and suitable for topical application to the hair. These anionic surfactants may be the same as, but are additional to and separate from, the anionic surfactants which may be used to form part of the composite particles.

Examples of suitable anionic cleansing surfactants are the alkyl sulphates, alkyl ether sulphates, alkaryl sulphonates, alkanoyl isethionates, alkyl succinates, alkyl sulphosuccinates, N-alkyl sarcosinates, alkyl phosphates, alkyl ether phosphates, alkyl ether carboxylates, alkyl ester carboxylates, and alpha-olefin sulphonates, especially their sodium, magnesium, ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule.

Typical anionic cleansing surfactants for use in shampoo compositions of the invention include sodium oleyl sulpho succinate, ammonium lauryl sulphosuccinate, ammonium lauryl sulphate, sodium cocoyl isethionate, sodium lauryl isethionate and sodium N-lauryl sarcosinate. The most preferred anionic surfactants are sodium lauryl sulphate, sodium lauryl ether sulphate(n)EO, (where n ranges from 1 to 3), ammonium lauryl sulphate and ammonium lauryl ether sulphate(n)EO, (where n ranges from 1 to 3).

The total weight of anionic cleansing surfactant in shampoo compositions of the invention is generally from 5 to 30, preferably from 6 to 20, more preferably from 8 to 16 percent by weight of the composition, excluding any anionic surfactant which may be present in the composite particles.

Co-Surfactant

The shampoo composition can optionally include co-surfactants, preferably an amphoteric or zwitterionic surfactant, which can be included in an amount ranging from 0 to about 8, preferably from 1 to 4 percent by weight of the composition.

Examples of amphoteric and zwitterionic surfactants include, alkyl betaines, alkyl amidopropyl betaines, alkyl sulphobetaines (sultaines), alkyl glycinates, alkyl carboxyglycinates, alkyl amphopropionates, alkylamphoglycinates, alkyl amidopropyl hydroxysultaines, acyl taurates and acyl glutamates, wherein the alkyl and acyl groups have from 8 to 19 carbon atoms. Typical amphoteric and zwitterionic surfactants for use in shampoos of the invention include lauryl amine oxide, cocodimethyl sulphopropyl betaine and preferably lauryl betaine, cocamidopropyl betaine and sodium cocamphopropionate.

Another preferred co-surfactant is a nonionic surfactant, which can be included in an amount ranging from 0 to 8, preferably from 2 to 5 percent, by weight of the composition.

For example, representative nonionic surfactants that can be included in shampoo compositions of the invention include condensation products of aliphatic ($C_8$-$C_{18}$) primary or secondary linear or branched chain alcohols or phenols with alkylene oxides, usually ethylene oxide and generally having from 6 to 30 ethylene oxide groups.

Further nonionic surfactants which can be included in shampoo compositions of the invention are the alkyl polyglycosides (APGs). Typically, the APG is one which comprises an alkyl group connected (optionally via a bridging group) to a block of one or more glycosyl groups. Preferred APGs are defined by the following formula:

$$RO-(G)_n$$

wherein R is a branched or straight chain $C_5$ to $C_{20}$ alkylor alkenyl group, G is a saccharide group and n is from 1 to 10.

Other sugar-derived nonionic surfactants which can be included in shampoo compositions of the invention include the $C_{10}$-$C_{18}$ N-alkyl ($C_1$-$C_6$) polyhydroxy fatty acid amides, such as the $C_{12}$-$C_{18}$ N-methyl glucamides, as described for example in WO 92 06154 and U.S. Pat. No. 5,194,639, and the N-alkoxy polyhydroxy fatty acid amides, such as $C_{10}$-$C_{18}$ N-(3-methoxypropyl) glucamide.

The shampoo composition can also optionally include one or more cationic co-surfactants included in an amount ranging from 0.01 to 10, more preferably from 0.05 to 5, most preferably from 0.05 to 2 percent by weight of the composition. Useful cationic surfactants are described hereinbelow in relation to conditioner compositions.

The total weight of surfactant (including any co-surfactant, and/or any emulsifier, but excluding any surfactant which may be present in the composite particles) in shampoo compositions of the invention is generally from 5 to 50, preferably from 5 to 30, more preferably from 10 to 25 percent by weight of the composition.

Cationic Polymer

The shampoo composition can optionally include cationic polymer(s), which are separate from the cationic polymers which may be used to form part of the composite particles and which are described above. Suitable cationic polymers for use in shampoo compositions of the invention are the same as those described above.

The cationic polymer will generally be present in compositions of the invention at levels of from 0.01 to 5, preferably from 0.05 to 1, more preferably from 0.08 to 0.5 percent by weight of the composition, excluding any cationic polymer which may be present in the composite particles.

Conditioner Compositions

Conditioning Surfactant

Conditioner compositions usually comprise one or more conditioning surfactants which are cosmetically acceptable and suitable for topical application to the hair.

Suitable conditioning surfactants are selected from cationic surfactants, used singly or in admixture. These cationic surfactants may be the same as, but are in addition to and separate from, the cationic surfactants which may be used to form part of the composite particles and which are described above.

Cationic surfactants useful in compositions of the invention contain amino or quaternary ammonium hydrophilic moieties which are positively charged when dissolved in the aqueous composition of the present invention.

Examples of suitable cationic surfactants are those corresponding to the general formula:

$$[N(R_1)(R_2)(R_3)(R_4)]^+(X)^-$$

in which $R_1$, $R_2$, $R_3$, and $R_4$ are independently selected from (a) an aliphatic group of from 1 to 22 carbon atoms, or (b) an aromatic, alkoxy, polyoxyalkylene, alkylamido, hydroxyalkyl, aryl or alkylaryl group having up to 22 carbon atoms; and X is a salt-forming anion such as those selected from halogen, (e.g. chloride, bromide), acetate, citrate, lactate, glycolate, phosphate nitrate, sulphate, and alkylsulphate radicals.

The aliphatic groups can contain, in addition to carbon and hydrogen atoms, ether linkages, and other groups such as amino groups. The longer chain aliphatic groups, e.g., those of about 12 carbons, or higher, can be saturated or unsaturated.

The most preferred cationic surfactants for conditioner compositions of the present invention are monoalkyl quaternary ammonium compounds in which the alkyl chain length is C16 to C22.

Examples of suitable cationic surfactants include quaternary ammonium compounds, particularly trimethyl quaternary compounds.

Preferred quaternary ammonium compounds include cetyltrimethylammonium chloride, behenyltrimethylammonium chloride (BTAC), cetylpyridinium chloride, tetramethylammonium chloride, tetraethylammonium chloride, octyltrimethylammonium chloride, dodecyltrimethylammonium chloride, hexadecyltrimethylammonium chloride, octyldimethylbenzylammonium chloride, decyldimethylbenzylammonium chloride, stearyldimethylbenzylammonium chloride, didodecyldimethylammonium chloride, dioctadecyldimethylammonium chloride, tallowtrimethylammonium chloride, cocotrimethylammonium chloride, PEG-2 oleylammonium chloride and salts of these, where the chloride is replaced by halogen, (e.g., bromide), acetate, citrate, lactate, glycolate, phosphate nitrate, sulphate, or alkylsulphate. Further suitable cationic surfactants include those materials having the CTFA designations Quaternium-5, Quaternium-31 and Quaternium-18. Mixtures of any of the foregoing materials may also be suitable. Particularly useful quaternary ammonium cationic surfactants for use in hair conditioners of the invention are cetyltrimethylammonium chloride, available commercially, for example as GENAMIN CTAC, ex Hoechst Celanese and Arquad 16/29 supplied by Akzo Nobel, and behenyltrimethylammonium chloride (BTAC) such as Genamin KDM-P supplied by Clariant. These may be the same as but are in addition to and separate from any quaternary ammonium compounds that may be used as charged organic molecule.

Further suitable cationic systems are primary, secondary, and tertiary fatty amines used in combination with an acid to provide the cationic species. These are the same as but are in addition to and separate from any such amines and acids that may be used as charged organic molecule. The alkyl groups of such amines preferably have from 12 to 22 carbon atoms, and can be substituted or unsubstituted.

Particularly useful are amido substituted tertiary fatty amines, in particular tertiary amines having one $C_{12}$ to $C_{22}$ alkyl or alkenyl chain. Such amines, useful herein, include stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide.

Also useful are dimethylstearamine, dimethylsoyamine, soyamine, myristylamine, tridecylamine, ethylstearylamine, N-tallowpropane diamine, ethoxylated (with 5 moles of ethylene oxide) stearylamine, dihydroxyethylstearylamine, and arachidyl behenylamine.

As stated previously, these amines are typically used in combination with an acid to provide the cationic species.

The preferred acid useful herein includes L-glutamic acid, lactic acid, hydrochloric acid, malic acid, succinic acid, acetic acid, fumaric acid, tartaric acid, citric acid, L-glutamic hydrochloride, and mixtures thereof; more preferably L-glutamic acid, lactic acid, citric acid. Cationic amine surfactants included among those useful in the present invention are disclosed in U.S. Pat. No. 4,275,055 to Nachtigal, et al., issued Jun. 23, 1981.

The molar ratio of protonatable amines to $H^+$ from the acid is preferably from about 1:0.3 to 1:1.2, and more preferably from about 1:0.5 to about 1:1.1.

In the conditioners of the invention, the level of cationic surfactant is preferably from 0.01 to 10, more preferably 0.05 to 5, most preferably 0.1 to 2 percent by weight of the total composition, excluding any cationic surfactant which may be present in the composite particles.

Fatty Materials

Conditioner compositions of the invention preferably additionally comprise fatty materials. The combined use of fatty materials and cationic surfactants in conditioning compositions is believed to be especially advantageous, because this leads to the formation of a structured lamellar or liquid crystal phase, in which the cationic surfactant is dispersed.

By "fatty material" is meant a fatty alcohol, an alkoxylated fatty alcohol, a fatty acid or a mixture thereof.

Preferably, the alkyl chain of the fatty material is fully saturated.

Representative fatty materials comprise from 8 to 22 carbon atoms, more preferably 16 to 22. Examples of suitable fatty alcohols include cetyl alcohol, stearyl alcohol and mixtures thereof. The use of these materials is also advantageous in that they contribute to the overall conditioning properties of compositions of the invention.

Alkoxylated, (e.g. ethoxylated or propoxylated) fatty alcohols having from about 12 to about 18 carbon atoms in the alkyl chain can be used in place of, or in addition to, the fatty alcohols themselves. Suitable examples include ethylene glycol cetyl ether, polyoxyethylene (2) stearyl ether, polyoxyethylene (4) cetyl ether, and mixtures thereof.

The level of fatty material in conditioners of the invention is suitably from 0.01 to 15, preferably from 0.1 to 10, and more preferably from 0.1 to 5 percent by weight of the total composition. The weight ratio of cationic surfactant to fatty alcohol is suitably from 10:1 to 1:10, preferably from 4:1 to 1:8, optimally from 1:1 to 1:7, for example 1:3.

Optional Ingredients

Suspending Agents

In a preferred embodiment, the hair treatment composition, especially if it is a shampoo composition, further comprises from 0.1 to 5 percent of a suspending agent, by weight of the total composition. Suitable suspending agents are selected from polyacrylic acids, cross-linked polymers of acrylic acid, copolymers of acrylic acid with a hydrophobic monomer, copolymers of carboxylic acid-containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 941 and Carbopol 980. An example of a suitable copolymer of a carboxylic acid containing a monomer and acrylic acid esters is Carbopol 1342. All Carbopol (trade mark) materials are available from Goodrich.

Suitable cross-linked polymers of acrylic acid and acrylate esters are Pemulen TR1 or Pemulen TR2. A suitable heteropolysaccharide gum is xanthan gum, for example that available as Kelzan mu.

Conditioning Agents

Silicone Conditioning Agents

The compositions of the invention can contain, emulsified droplets of a silicone conditioning agent, for enhancing conditioning performance.

Suitable silicones include polydiorganosiloxanes, in particular polydimethylsiloxanes which have the CTFA designation dimethicone. Also suitable for use compositions of the invention (particularly shampoos and conditioners) are polydimethyl siloxanes having hydroxyl end groups, which have the CTFA designation dimethiconol. Also suitable for use in compositions of the invention are silicone gums having a slight degree of cross-linking, as are described for example in WO 96/31188.

The viscosity of the emulsified silicone itself (not the emulsion or the final hair conditioning composition) is typically at least 10,000 mm$^2$s$^{-1}$ at 25° C. the viscosity of the silicone itself is preferably at least 60,000 mm$^2$s$^{-1}$, most preferably at least 500,000 mm$^2$s$^{-1}$, ideally at least 1,000,000 mm$^2$s$^{-1}$. Suitable methods for measuring viscosity of viscous materials are given in "Corporate Test Method 004", Dow Corning Corporation, Jul. 29, 1970.

Emulsified silicones for use in the shampoo compositions of the invention will typically have an average silicone droplet diameter in the composition of less than 30, preferably less than 20, more preferably less than 10 microns, ideally from 0.01 to 1 microns. Silicone emulsions having volume-based median silicone droplet diameter ($D_{0.5}$) of $\leq$0.15 microns are generally termed microemulsions.

Examples of suitable pre-formed emulsions include emulsions DC2-1766, DC2-1784, DC-1785 DC-1786 and microemulsions DC2-1865 and DC2-1870, all available from Dow Corning. These are all emulsions/microemulsions of dimethiconol. Cross-linked silicone gums are also available in a pre-emulsified form, which is advantageous for ease of formulation. A preferred example is the material available from Dow Corning as DC X2-1787, which is an emulsion of cross-linked dimethiconol gum. A further preferred example is the material available from Dow Corning as DC X2-1391, which is a microemulsion of cross-linked dimethiconol gum.

A further preferred class of silicones for inclusion in compositions of the invention are amino functional silicones. By "amino functional silicone" is meant a silicone containing at least one primary, secondary or tertiary amine group, or a quaternary ammonium group. Examples of suitable amino functional silicones include: polysiloxanes having the CTFA designation "amodimethicone".

Specific examples of amino functional silicones suitable for use in the invention are the aminosilicone oils DC2-8220, DC2-8166, DC2-8466, and DC2-8950-114 (all ex Dow Corning), and GE 1149-75, (ex General Electric Silicones).

Suitable quaternary silicone polymers are described in EP-A-0 530 974. A preferred quaternary silicone polymer is K3474, ex Goldschmidt.

Also suitable are emulsions of amino functional silicone oils with non ionic and/or cationic surfactant as emulsifiers. Pre-formed emulsions of amino functional silicone are also available from suppliers of silicone oils such as Dow Corning and General Electric. Specific examples include DC929 Cationic Emulsion, DC939 Cationic Emulsion, and the non-ionic emulsions DC2-7224, DC2-8467, DC2-8177 and DC2-8154 (all ex Dow Corning).

With shampoos it is particularly preferred to use a combination of amino and non amino functional silicones.

The total weight of silicone is preferably from 0.01 to 10, more preferably from 0.3 to 5, most preferably 0.5 to 3 percent by weight of the total composition.

Non-Silicone Oily Conditioning Components

Compositions according to the present invention may also comprise a dispersed, non-volatile, water-insoluble oily conditioning agent.

By "insoluble" is meant that the material is not soluble in water (distilled or equivalent) at a concentration of 0.1% (w/w), at 25° C.

Suitable oily or fatty materials are selected from hydrocarbon oils, fatty esters and mixtures thereof. Straight chain hydrocarbon oils will preferably contain from about 12 to about 30 carbon atoms. Also suitable are polymeric hydrocarbons of alkenyl monomers, such as $C_2$-$C_6$ alkenyl monomers.

Specific examples of suitable hydrocarbon oils include paraffin oil, mineral oil, saturated and unsaturated dodecane, saturated and unsaturated tridecane, saturated and unsaturated tetradecane, saturated and unsaturated pentadecane, saturated and unsaturated hexadecane, and mixtures thereof. Branched-chain isomers of these compounds, as well as of higher chain length hydrocarbons, can also be used.

Specific examples of suitable mineral oils are preferably those having a low viscosity and/or low molecular weight, typically a molecular weight below 600 Da (eg, from 120 to 600 Da) and/or a viscosity below 4 mm$^2$s$^{-1}$. Suitable methods for measuring viscosity of viscous materials are given in "Corporate Test Method 004", Dow Corning Corporation, Jul. 29, 1970. For example, oils comprising straight chain or branched chain, saturated or unsaturated hydrocarbons having from 10 to 44 carbon atoms, optionally comprising one or more phenyl groups, are advantageously preferred.

Functionalised oils, preferably compounds containing one or more groups selected from ether, ester, keto, aldehyde, carboxyl, alcohol, diol, polyol, amino, amido, thiol, thioether, and preferably containing 8 to 44 carbon atoms are suitable; specific examples are isoamyl ether, isopropyl myristate, octan-2-one, decyl alcohol and 1,10-decanediol; saccharide polyesters (eg, esters of sucrose with carboxylic acids having from 4 to 36 carbon atoms, such as sucrose pentaerucate).

Suitable fatty esters are characterised by having at least 10 carbon atoms, and include esters with hydrocarbyl chains derived from fatty acids or alcohols, monocarboxylic acid esters include esters of alcohols and/or acids of the formula R'COOR in which R' and R independently denote alkyl or alkenyl radicals and the sum of carbon atoms in R' and R is at least 10, preferably at least 20. Di- and trialkyl and alkenyl esters of carboxylic acids can also be used.

Particularly preferred fatty esters are mono-, di- and triglycerides, more specifically the mono-, di-, and tri-esters of glycerol and long chain carboxylic acids such as $C_1$-$C_{22}$ carboxylic acids. Preferred materials include cocoa butter, palm stearin, sunflower oil, soyabean oil and coconut oil.

The oily or fatty material is suitably present at a level of from 0.05 to 10, preferably from 0.2 to 5, more preferably from about 0.5 to 3 percent by weight of the composition.

EXAMPLES

The invention will now be further illustrated by the following, non-limiting Examples, in which parts and percentages are by weight.

Example 1

Preparation of Complexed Clay Particles

Complexed clay particles P1, P2, P3 and P4 were prepared from the raw materials shown in Table 1. The levels of raw materials are expressed as 100% active.

TABLE 1

| Component | P1 | P2 | P3 | P4 | P5 | P6 |
|---|---|---|---|---|---|---|
| charged organic molecule | | | | | | |
| CTAC | 1.97 | 5.92 | — | — | — | — |
| BTAC | — | — | 1.97 | 5.92 | — | — |
| cationic guar (Jaguar CBS) | — | — | — | — | 1.97 | — |
| Montaline C40 clay | — | — | — | — | — | 5.92 |
| synthetic clay (hectorite) | 3.95 | 11.85 | 3.95 | 11.85 | 3.95 | 11.85 |
| other | | | | | | |
| demineralised water | to 100 | to 100 | to 100 | to 100 | to 100 | to 100 |

The charged organic molecule was added to the demineralised water and heated to 60° C. with stirring (at speed setting 3-4 on a Silverson mixer, such as a Silverson L4R, ex-Silverson) for 30 minutes until it had dissolved. The resulting dispersion was allowed to cool to 30 to 35° C. The clay was then added into the cooled dispersion in powder form and mixed for 15 minutes (at speed setting 3-4 on a Silverson mixer). The product obtained was a suspension of white particles in water.

Comparative Examples A, B and C

The following Comparative Examples (i.e. not according to the invention) were prepared as shown in Tables 2 to X below:

Comparative Example A basic hair conditioner.

Comparative Example B hair conditioner containing synthetic clay (Laponite XLS).

TABLE A

Materials used in the examples.

| Chemical | Active level | Trade Name | Supplier |
|---|---|---|---|
| Silicone emulsion (dimethicone) | 60% | DC1785 | Dow Corning |
| Behenyltrimethyl ammonium chloride (BTAC) | 85% | *Genamin KDMP | Clariant |
| Cetearyl alcohol | 100% | *Laurex CS | Ellis & Everard |
| Methyl paraben | 100% | *Nipagen M | Chemlink Specialities |
| Synthetic clay (hectorite) | 100% | *Laponite XLS | Laporte |
| Quaternium 18 bentonite | 100% | *Tixogel MP100 | Sud Chemie |
| Cetyltrimethyl ammonium chloride (CTAC) | 29% | Arquad 16/29 | Akzo Nobel |
| Cocammonium carbanoyl chloride | 40% | Montaline C40 | Seppic |
| Cationic guar | 100% | Jaguar CBS | Rhodia |
| Perfume | 100% | — | — |
| Sodium Lauryl Ether Sulphate (SLES) | 28% | Empicol ESB 28 | Albright & Wilson |
| Cocoamidopropyl Betaine (CAPB) | 30% | Tegobetaine CK | Goldschmidt |
| Sodium Chloride | 100% | — | Aldrich |

*Trade Mark

Comparative Example C hair conditioner containing commercially available hydrophobically modified clay (Quaternium 18 bentonite).

Comparative Examples A, B and C were prepared according to the formulations given in Table 2. The levels are expressed as 100% active.

TABLE 2

| Chemical name | weight % | | |
|---|---|---|---|
| | A | B | C |
| silicone ex-emulsion DC1785 | 1.0 | 1.0 | 1.0 |
| BTAC | 2.0 | 2.0 | 2.0 |
| cetearyl alcohol | 4.0 | 4.0 | 4.0 |
| methyl paraben | 0.2 | 0.2 | 0.2 |
| Perfume | 0.6 | 0.6 | 0.6 |
| Synthetic clay (hectorite) | — | 0.67 | — |
| Quaternium 18 bentonite | — | — | 1.0 |
| Demineralised water | to 100 | to 100 | to 100 |

Comparative example A was prepared by first heating the water to above 85° C. The methyl paraben was then added with stirring using a Silverson mixer at speed 9-10, until it dissolved. The BTAC and Cetearyl alcohol were melted together and added to the aqueous methyl paraben solution under high shear (Silverson mixer at speed 9-10). The high shear was continued for 3 minutes and then allowed to cool to room temp under low shear (using a Heidolph mixer, such as a Heidolph RZ R2100). Silicone emulsion was then added with mixing.

Comparative Example B was prepared using the method described for Comparative Example A, but with the additional step of adding the synthetic clay (Laponite XLS), in powder form, at the end with the silicone, and mixing until dispersed throughout the conditioner.

Comparative Example C was prepared as follows:

The demineralised water was heated to above 85° C. and the methyl paraben added under high shear (Silverson mixer at speed 9-10) until it dissolved. The BTAC and Cetearyl alcohol were melted together and the Quaternium 18 bentonite dispersed into the melt. The resulting dispersion was then added to the aqueous methyl paraben solution under high shear. The high shear was continued for 3 minutes and the mixture was then allowed to cool to room temp under low shear. The silicone emulsion was then added with mixing.

Examples 2 to 7

Hair Conditioner Compositions Containing Complexed Clay Particles

Conditioner compositions containing complexed clay particles were prepared by addition of the aqueous dispersions of composite particles (P1, P2, P3, P4, P5 or P6) to conditioner ingredients, to give the compositions shown in Table 3 below (Examples 2 to 7). Comparative example A (the conditioner formulation given in Table 2) is also shown, which contains no composite particles. Amounts are expressed as weight % of 100% active ingredient, based on the weight of the total composition. The method of preparation of Examples 2 to 7 is given at the foot of Table 3.

TABLE 3

| | Example | | | | | | |
|---|---|---|---|---|---|---|---|
| | 2 | 3 | 4 | 5 | 6 | 7 | A |
| Conditioner | | | | | | | |
| Silicone ex. DC1785 | 1.0 | 1.0 | 1.0 | 1.0 | 1.0 | 1.0 | 1.0 |
| BTAC (I) | 2.0 | 2.0 | 2.0 | 2.0 | 2.0 | 2.0 | 2.0 |
| Cetearyl alcohol | 4.0 | 4.0 | 4.0 | 4.0 | 4.0 | 4.0 | 4.0 |
| Methyl paraben | 0.2 | 0.2 | 0.2 | 0.2 | 0.2 | 0.2 | 0.2 |
| Perfume | 0.6 | 0.6 | 0.6 | 0.6 | 0.6 | 0.6 | 0.6 |
| demineralised water (I) | 75.41 | 75.41 | 75.41 | 75.41 | 75.41 | 75.41 | 92.2 |
| complexed clay particles | P1 | P2 | P3 | P4 | P5 | P6 | — |
| CTAC | 0.33 | 0.99 | — | — | — | — | — |
| BTAC (II) | — | — | 0.33 | 0.99 | — | — | — |
| cationic polymer (Jaguar) | — | — | — | — | 0.33 | — | — |
| Montaline C40 | — | — | — | — | — | 0.99 | — |
| synthetic clay (hectorite) | 0.66 | 1.99 | 0.66 | 1.99 | 0.66 | 1.99 | — |
| demineralised water (II) | 15.8 | 13.81 | 15.8 | 13.81 | 15.8 | 13.81 | — |
| total | 100 | 100 | 100 | 100 | 100 | 100 | 100.00 |

The conditioner compositions containing complexed clay particles (Examples 2 to 7) were prepared as follows:

The demineralised water (I) was heated to above 85° C. and the methyl paraben added with stirring until it dissolved. The BTAC (I) and Cetearyl alcohol were melted together and added to the aqueous methyl paraben solution under high shear using a Silverson mixer at speed 9-10. The high shear was continued for 3 minutes and the suspension of composite particles (P1, P2, P3, P4, P5 or P6) was well shaken before being added under low shear (using a Heidolph mixer). The mixture was then allowed to cool to room temp under low shear. The silicone emulsion was then added with mixing.

Example 8

Preparation of Basic Shampoo

A basic hair shampoo was prepared according to the formulation shown in Table 4. Weight percents are of the chemicals as 100% active and based on the weight of the total composition.

TABLE 4

| Chemical name | Weight % |
| --- | --- |
| SLES | 14.0 |
| CAPB | 2.0 |
| demineralised water | 82.5 |
| sodium chloride | 1.5 |
| Total | 100 |

The shampoo was prepared by mixing the ingredients together under medium shear (Silverson mixer at number 3-4).

Example 9

Evaluation of Hair Friction

European dark brown hair was used in switches of 2.5 g weight and 6 inches length.

Each composition was tested on 5 such hair switches.

Friction Measurement Methodology

All friction measurements were carried out under controlled conditions of 20° C. and 50% RH.

Friction was measured using a TA.XT2i Texture Analyser supplied by Stable Micro Systems, Surrey, UK. The friction probe was a stainless steel cylinder, which was coated with rubber material. The weight of the probe was approximately 60 g. When in use, an area of contact between the friction probe and the hair of approximately 1.0 cm$^2$ was achieved.

The methodology used to assess the friction properties of hair treated with conditioner compositions was as follows:

A switch of hair was securely mounted onto the texture analyser, the hair fibres being aligned with combing before being secured. The friction probe was placed onto the hair and moved along the hair at a speed of 10 mms$^{-1}$ to measure the friction between the probe and the hair. 2 measurements were performed per switch and 5 switches per composition were tested.

Treatment of Hair with Shampoo

Hair switches were first washed with the basic shampoo composition given in Table 4 above (which is not a shampoo according to the invention and as such contains no composite particles) according to the following protocol:

Each switch was first rinsed under running tap water for 30 seconds. Shampoo (0.5 ml) was applied to each switch and the hair agitated with gloved fingers for 30 seconds followed by further rinsing for 30 seconds under running tap water.

The friction value of each wet switch was then measured using the texture analyser as described above. The switches were then dried at 50° C. for 30 minutes and the friction re-measured using the texture analyser to obtain the dry friction value.

Treatment of Hair with Conditioners

Each hair switch, after the procedure above, was then treated with conditioner compositions as follows:

Each switch was first rinsed under running tap water for 10 seconds before conditioner (0.5 ml) was applied and massaged into the hair for 1 minute. The conditioner was then left on the hair for 1 minute without agitation before being rinsed under running tap water for 30 seconds. The texture analyser was then used to measure the friction of the wet switch. Again, following this measurement, the hair was dried at 50° C. and the friction measured again to obtain the dry friction value.

The reduction in the friction of the shampooed hair as a result of treatment with the conditioner compositions was calculated as the difference in the friction value of each hair switch after shampooing and that of the hair switch after treatment with the conditioner compositions. This difference was then expressed as a percentage of the friction value of the shampooed hair. This calculation was performed for the wet and dry hair switches.

Two separate sets of experiments were performed:

Set 1) Examples 2 to 7 and Comparative Example A; wet and dry friction measured, and Set 2) Example 2 and Comparative Examples A, B and C; wet friction measured.

Due to the nature of the experiments, results are only comparable within a single set of experiments and not between separate sets.

The percent reduction in friction thus calculated for the wet and dry hair switches treated with conditioner compositions (an average of 5 switches per composition) are shown in Tables 5 (Examples 2 to 7 and Comparative Example A) and 6 (Example 2 and Comparative Examples A, B and C) below.

TABLE 5

| Example | % reduction in friction (wet) | % reduction in friction (dry) |
| --- | --- | --- |
| A | 50.4 | 25.5 |
| 2 | 64.2 | 43.2 |
| 3 | 60.1 | 41.3 |
| 4 | 54.4 | 28.1 |
| 5 | 55.4 | 32.4 |
| 6 | 57.1 | 24.5 |
| 7 | 53.5 | 34.1 |

It will be seen that both wet and dry friction of hair was dramatically reduced by use of the conditioner compositions in accordance with the invention. In all cases, an additional benefit was seen over Comparative Example A.

TABLE 6

| Example | % reduction in friction (wet) |
| --- | --- |
| A | 57.2 |
| B | 50.9 |
| C | 59.2 |
| 2 | 65.3 |

It will be seen that wet friction of hair was dramatically reduced by use of the conditioner composition in accordance with the invention and an additional benefit was seen over Comparative Examples A, B and C.

Example 10

Evaluation of Hair Feel by Consumers

The hair used in the evaluation of hair feel was dark brown human hair in switches of approximately 11 inches in length and approximately 10 g in weight. Before use, the switches were balanced with respect to the feel attributes that were to be assessed, namely slippery feel, smooth feel and, moisturised feel, such that there were no significant differences in these feel attributes between the switches.

The hair switches were cleaned prior to treatment with the conditioner compositions as follows: they were wetted with running tap water for 10 s. The shampoo given in Table 4, which contains no composite particles, (0.14 g shampoo per g hair) was dosed onto each switch and massaged for 30 s before being rinsed for 30 s.

Conditioner composition (0.14 g conditioner per g hair) was then applied to the washed, wet hair and massaged for 1 minute. The conditioner was left on the hair for 1 minute without agitation and rinsed under running tap water for 30 s. The switches were then allowed to dry. One switch per conditioner composition was used.

In this way, hair switches were treated with Examples 3 and 5 and Comparative Example A before being evaluated for slippery feel, smooth feel and moisturised feel by a panel of 10 consumers. The consumers used a sliding scale from 0 to 100 to evaluate each feel attribute for each composition.

The scores are shown in Table 7 below and are an average of the assessments by the 10 consumers.

TABLE 7

| Example | Feel attribute | | |
|---|---|---|---|
| | Slippery | Smooth | Moisturised |
| A | 44.10 | 44.10 | 48.20 |
| 3 | 70.50 | 72.50 | 74.10 |
| 5 | 59.20 | 53.90 | 59.10 |

It will be seen that feel attributes are significantly increased on hair treated with conditioner compositions according to the invention, compared to hair treated with Comparative Example A.

The invention claimed is:

1. A process for the preparation of a hair treatment composition comprising an aqueous dispersion of composite particles, wherein the particles comprise:
   i) an anionic smectic clay with a net negative surface charge, and
   ii) a charged organic molecule having a positive charge that is the cation of an alkyl trimethyl ammonium chloride containing a straight chain or branched alkyl group that comprises from 12 to 22 carbon atoms, wherein the charged organic molecule is not capable of imparting a colour to hair, the process comprising the steps of:
   (a) mixing an aqueous dispersion of the charged organic molecule with the clay to form an aqueous dispersion of composite particles, wherein said aqueous dispersion of composite particles is substantially free from non-ionic surfactant, and
   (b) combining the aqueous dispersion of composite particles with suitable hair treatment ingredients in a compatible aqueous carrier,
   wherein the hair treatment composition is in the form of a post-wash rinse-off conditioner that further comprises (I) emulsified droplets of a silicone conditioning agent and (II) at least 50% by weight, based on the weight of the total composition, of water; and wherein the weight ratio of the charged organic molecule to the clay is from 0.1:1 to 10:1; and wherein the composite particles have a volume-based median particle diameter ($D_{0.5}$) of from greater than 2 to less than 50 microns; and wherein the anionic smectic clay has a cation exchange capacity of from 30 meq/100 g to 100 meq/100 g.

2. A process as claimed in claim 1, wherein the clay is a synthetic hectorite.

3. A process as claimed in claim 1, wherein the weight of composite particles, based on the total composition, is from 0.01 to 20 percent by weight of the total composition.

4. A process as described in claim 1 wherein the weight ratio of the charged organic molecule to the clay is from 0.2:1 to 5:1.

5. A process as claimed in claim 1, wherein the clay has a volume based median particle diameter of from 0.02 μm to 20 μm.

6. A process for the preparation of a hair treatment composition comprising an aqueous dispersion of composite particles, wherein the particles comprise:
   i) a cationic clay with a net positive surface charge, and
   ii) a charged organic molecule having a negative charge that is the anion of an anionic surfactant selected from the group consisting of alkyl sulphates, alkyl ether sulphates, alkaryl sulphonates, alkanoyl isethionates, alkyl succinates, alkyl sulphosuccinates, alkyl phosphates, alkyl ether phosphates, alkyl carboxylates, alkyl ether carboxylates, alkyl ester carboxylates, N-alkyl sarcosinates, and alpha-olefin sulfonates, and the sodium, magnesium ammonium and mono-di- and triethanol amine salts thereof, wherein the alkyl and acyl groups thereof comprise from 12 to 22 carbon atoms, wherein the charged organic molecule is not capable of imparting a color to the hair, the process comprising the steps of:
   (a) mixing an aqueous dispersion of the charged organic molecule with the clay to form an aqueous dispersion of composite particles, wherein said aqueous dispersion of composite particles is substantially free from non-ionic surfactant, and
   (b) combining the aqueous dispersion of composite particles with suitable hair treatment ingredients in a compatible aqueous carrier,
   wherein the hair treatment composition is in the form of a post-wash rinse-off conditioner that further comprises (I) emulsified droplets of a silicone conditioning agent and (II) at least 50% by weight, based on the weight of the total composition, of water; and wherein the weight ratio of the charged organic molecule to the clay is from 0.1:1 to 10:1; and wherein the composite particles have volume-based median particle diameter ($D_{0.5}$) of from greater than 2 to less than 50 microns; and wherein the cationic clay has a cation exchange capacity of from 30 meq/100 g to 200 meq/100 g and comprises a hydrotalcite.

7. A process as claimed in claim 1 wherein the alkyl trimethyl ammonium chloride contains an alkyl group that comprises from 16 to 22 carbon atoms.

8. A process as claimed in claim 1 wherein the anionic smectic clay is selected from the group consisting of montmorillonites, hectorites, volchonskoites, nontronites, saponites, beidelites and sauconites.

9. A process for the preparation of a hair treatment composition comprising an aqueous dispersion of composite particles, wherein the particles comprise:

i) an anionic smectic clay with a net negative surface charge, and
ii) a charged organic molecule having a positive charge that is the cation of a cationic surfactant that comprises cetyl trimethylammonium chloride, wherein the charged organic molecule is not capable of imparting a colour to hair, the process comprising the steps of:
(a) mixing an aqueous dispersion of the charged organic molecule with the clay to form an aqueous dispersion of composite particles, wherein said aqueous dispersion of composite particles is substantially free from non-ionic surfactant, and
(b) combining the aqueous dispersion of composite particles with suitable hair treatment ingredients in a compatible aqueous carrier, wherein the hair treatment composition is in the form of a post-wash rinse-off conditioner that further comprises (I) emulsified droplets of a silicone conditioning agent and (II) at least 50% by weight, based on the total weight of the composition, of water; and wherein the weight ratio of the charged organic molecule to the clay is from 0.1:1 to 10:1; and wherein the composite particles have a volume-based median particle diameter ($D_{0.5}$) of from greater than 2 to less than 50 microns; and wherein the anionic smectic clay has a cation exchange capacity of from 30 meq/100 g to 100 meq/100 g.

10. A process as claimed in claim 9 wherein the anionic smectic clay comprises hectorite.

\* \* \* \* \*